US006410039B1

(12) United States Patent
Walker

(10) Patent No.: US 6,410,039 B1
(45) Date of Patent: Jun. 25, 2002

(54) PROTECTIVE TOPICAL COMPOSITION, PRODUCTS INCLUDING THE SAME, AND METHODS

(75) Inventor: Edward B. Walker, Ogden, UT (US)

(73) Assignee: First Scientific, Inc., Ogden, UT (US)

( * ) Notice: Subject to any disclaimer, the term of this patent is extended or adjusted under 35 U.S.C. 154(b) by 0 days.

(21) Appl. No.: 09/396,580

(22) Filed: Sep. 15, 1999

(51) Int. Cl.$^7$ ............................................... A01N 25/34
(52) U.S. Cl. ....................... 424/404; 424/402; 514/844; 514/938
(58) Field of Search ................................. 424/436, 443, 424/449, 404, 402; 514/844, 938

(56) References Cited

U.S. PATENT DOCUMENTS

| | | | |
|---|---|---|---|
| 4,689,168 A | * | 8/1987 | Requejo ..................... 252/139 |
| 4,708,813 A | * | 11/1987 | Snyder |
| 4,725,489 A | * | 2/1988 | Jones et al. ................. 428/289 |
| 4,803,233 A | | 2/1989 | Narula et al. |
| 4,806,572 A | | 2/1989 | Kellett |
| 4,904,524 A | | 2/1990 | Yoh |
| 5,182,105 A | | 1/1993 | Takata et al. |
| 5,518,647 A | | 5/1996 | Zocchi |
| 5,518,716 A | | 5/1996 | Riccio et al. |
| 5,549,836 A | | 8/1996 | Moses |
| 5,578,298 A | | 11/1996 | Berthiaume et al. |
| 5,589,177 A | | 12/1996 | Herb et al. |
| 5,656,280 A | | 8/1997 | Herb et al. |
| 5,759,530 A | | 6/1998 | Riccio et al. |
| 5,763,332 A | | 6/1998 | Gordon et al. |
| 5,830,483 A | | 11/1998 | Seidel et al. |
| 5,879,684 A | | 3/1999 | Fox |
| 5,965,115 A | * | 10/1999 | Bolich, Jr. et al. ....... 424/70.12 |

OTHER PUBLICATIONS

Skin Protectant Drug Products for Over–the–Counter Human Use: Tentative Final Monograph, Federal Register, vol. 48, No. 32, Feb. 15, 1983 pp. 6820–6833.

* cited by examiner

Primary Examiner—Thurman K. Page
Assistant Examiner—Humera N. Sheikh
(74) Attorney, Agent, or Firm—TraskBritt

(57) ABSTRACT

A topical composition with silicone oil emulsified in water. The topical composition may be made by diluting a concentrated silicone oil-in-water emulsion with water. The silicone oil of the topical composition and of the concentrated silicone oil-in-water emulsion is suspended in the water by one or more non-ionic surfactants. A combination of non-ionic surfactants may be employed. The topical composition may also include a blend of preservatives, which may be selected to have a synergistic effect. The silicone oil constitutes about 35% of the weight of the concentrated silicone oil-in-water emulsion. The non-ionic surfactant or surfactants make up about 3.5% of the weight of the concentrated oil-in-water emulsion. The diluted topical composition may contain silicone oil in amounts of about 0.1 to about 35%, preferably less than 3% down to about 1%, and more preferably about 1 to about 2% of the weight of the topical composition. The invention also includes wipe sheets wetted or impregnated with the topical composition. The topical composition can be applied to skin by way of a wet wipe, by spraying, or by rubbing into the skin.

26 Claims, No Drawings

PROTECTIVE TOPICAL COMPOSITION, PRODUCTS INCLUDING THE SAME, AND METHODS

BACKGROUND OF THE INVENTION

1. Field of the Invention

The present invention relates to topical compositions that are therapeutic to or protect skin. Particularly, the present invention relates to topical compositions that include an emulsion of silicone oil in water and to wet wipes including the topical compositions. More particularly, the present invention relates to topical compositions having non-ionic surfactants that suspend silicone oil in water, to wet wipe products including the topical compositions, and to methods of applying the topical compositions to skin.

2. State of the Art

Skin treatment and protection products, such as body lotions and washing compositions, are used to clean skin, to treat adverse conditions of the skin, such as dermatitis, and to prevent irritations to and adverse conditions of the skin. Some of these skin treatment and protection products contain ingredients that protect the skin, such as oils. In water-based, or aqueous skin treatment and protection products that include oils, the oils are typically suspended in an aqueous carrier solution with surfactants, or emulsifiers, by way of an emulsion.

Babies, incontinent adults, and bedridden patients are particularly susceptible to irritations in the perineal area, such as contact dermatitis, which is typically referred to as "diaper rash". Perineal dermatitis is thought to be caused by contact with bodily waste, such as urine and feces. Symptoms of perineal dermatitis include erythema, swelling, oozing, vesication, crusting and scaling, with the possibility of excoriation, thickening, and hyperpigmentation over time. One of the best ways to treat and prevent perineal dermatitis is to apply a protective barrier to the skin to protect it from bodily waste.

There are many commercially available protective barrier materials or compositions that can be topically applied to skin. These protective barrier materials or compositions can be in the form of powders, lotions, creams and ointments. Protective barrier materials or compositions can be sprinkled onto the skin, rubbed into the skin, or wiped onto the skin with a material impregnated with the protective barrier material or composition, such as a wet wipe towelette. Wet wipe towelettes are typically formed from combinations of cellulosic fibers, synthetic polymeric fibers, such as polyester, polypropylene, and binders. Wet wipe towelettes are generally premoistened with a composition that contains water with lesser amounts of ingredients such as moistening agents or humectants, emollients, surfactants, emulsifiers, antimicrobial agents, skin protectants, pH adjusting agents, fragrances, and powders.

In order to effectively treat and protect skin, the protective barrier material or composition must prevent prolonged exposure of the skin to irritants, such as body waste, without substantially reducing the rate at which moisture is lost through the skin. In addition, an effective amount of an effective barrier material or composition must be applied to the skin. It is known in the art that homogeneous compositions that contain protective barrier materials or compositions facilitate the homogeneous distribution of the protective barrier materials or compositions on the wipe. Upon applying a homogenous composition to the skin with such a wipe, the homogeneous distribution of protective barrier materials or compositions on the wipe facilitates the application of an effective amount of the protective barrier materials or compositions to the skin.

When a skin treatment and protection product is an oil-in-water emulsion of an oil-based protective barrier material or composition in water, the product will typically include surfactants, or emulsifiers, to suspend the protective barrier material or composition in the water in a manner that forms a homogenous emulsion. Surfactants, which typically include lipophilic (i.e., "fat loving") tails and hydrophilic (i.e., "water loving") heads, reduce the surface tension at the interface between particles of oil-based materials or compositions and water.

It is also known to include a preservative in oil-in-water emulsions of skin treatment and protection products to minimize unwanted microbial growth. A wide variety of preservatives are commercially available, including the mixture of 5-chloro-2-methyl-4-isothiazolin-3-one and 2-methyl-4-isothiazolin-3-one, available under the trade names KATHON® and ISOCIL®, other chlorinated and non-chlorinated methylisothiazolinones, sorbic acid or a salt thereof, parabens, as well as other known preservatives.

Topical care compositions including water, a silicone oil, and an emulsifier to suspend the silicone oil in the water are known. Exemplary topical compositions including these constituents are disclosed in U.S. Pat. No. 5,648,083 (hereinafter "the '083 Patent"), issued to Blieszner et al. on Jul. 15, 1997, and in U.S. Pat. No. 5,043,155 (hereinafter "the '155 Patent"), issued to Puchalski et al. on Aug. 27, 1991.

The '083 Patent discloses a silicone oil-in water emulsion composition and a wipe product including the emulsion composition. The disclosed amounts of silicone oil that are useful in the emulsion composition of the '083 Patent are from about 0.5% to less than about 3% of the total weight of the emulsion composition. The '083 Patent also discloses the use of carboxylic acid polymeric emulsifiers to suspend the silicone oil in the water. As those of skill in the art are aware, carboxylic acid polymeric emulsifiers are ionic surfactants and, in particular, anionic surfactants. Due to the ionic nature of carboxylic acid polymeric emulsifiers, their use is somewhat undesirable since the ability of these emulsifiers to suspend a droplet of hydrophobic material in an aqueous solution depends upon the pH of the aqueous solution. If the pH of the solution drops or increases outside of the effective pH range for an ionic emulsifier, the hydrophobic material will no longer be suspended in the aqueous solution. As a result, the emulsion will separate.

Alternative emulsifiers that may be used in the emulsion composition of the '083 Patent are disclosed in the '155 Patent, the disclosure of which is incorporated by reference into the '083 Patent.

The '155 Patent discloses an emulsion composition that includes water, silicone oil, and an amphipathic emulsifier. The emulsifier comprises about 0.02–2.0% of the weight of the emulsion composition. The silicone oil comprises about 3–40% of the emulsion composition by weight.

Since the emulsion composition of the '155 Patent comprises such a high concentration of silicone oil, the emulsion composition must be manufactured using high shearing processes. First, the silicone oil and the emulsifier are blended by high shear mixing processes. Next, as the high shear mixing processes continue, water is gradually added in small volumes to the silicone oil and emulsifier mixture. As the water is added, the silicone oil and the emulsifier molecules form micelles that are suspended in the water.

The high concentration of silicone oil in the emulsion composition disclosed in the '155 Patent is somewhat undesirable since, after applying the emulsion composition to the skin and upon evaporation of the water of the emulsion composition and the resultant release of the silicone oil from the micelles, the silicone oil will leave a greasy or oily residue on the skin.

Moreover, the use of a maleic anhydride and octadecene polymer, the non-ionic amphipathic emulsifier disclosed as being useful in the emulsion composition of the '155 Patent, is somewhat undesirable in a topical composition since maleic anhydride is irritating to tissues such as skin. The other emulsifiers that are disclosed in the '155 Patent as being useful in the emulsion composition thereof are acidic, or anionic, emulsifiers and include different carbomers, which are polymers of acrylic acid crosslinked with allyl sucrose, and $C_{12}$–$C_{22}$ alkyl-substituted acrylic acid copolymers. Due to the ionic nature of these emulsifiers, their use is somewhat undesirable since the ability of these emulsifiers to suspend a droplet of hydrophobic material in an aqueous solution depends upon the pH of the aqueous solution. If the pH of the solution drops or increases outside of the effective pH range for an ionic emulsifier, the hydrophobic material will no longer be suspended in the aqueous solution. As a result, the emulsion will separate.

As those of skill in the art are aware, the pH of a solution may change significantly over periods of days, weeks, months, or years. Following the manufacture of topical compositions, including those with which wet wipes are wetted, the topical compositions and products including the same are typically warehoused, transported, stored, and placed on the shelf of a retailer. Accordingly, after the topical compositions are manufactured, a very long period of time may pass before the wet wipes or topical compositions are actually used by a consumer. Thus, without a pH adjusting agent, it is very likely that the pH of the topical composition will change significantly from the manufacture thereof to the use thereof.

The art does not include a topical composition that includes a therapeutic or protective amount of silicone oil emulsified in an aqueous solution by a non-irritating surfactant that will retain the silicone oil in solution over long periods of time, even with significant changes in the pH of the aqueous solution.

SUMMARY OF THE INVENTION

A topical composition of water, silicone oil, and one or more non-ionic surfactants to suspend the silicone oil in the water is disclosed. The silicone oil is suspended in the water by the non-ionic surfactants to form an oil-in-water emulsion.

Silicone oil preferably makes up less than 3% down to about 0.1% of the weight of the topical composition, but may comprise as much as 35% of the weight of the topical composition when the topical composition is used with a sheet to form a wet wipe. More preferably, silicone oil comprises less than 3% down to about 1% of the weight of the topical composition. Topical compositions including about 1 to about 2% by weight of the topical composition are even more preferred. These amounts of silicone oil will therapeutically benefit and protect the skin, but are not as likely as compositions containing greater amounts of silicone oil to leave an oily or greasy residue on the skin. An example of a silicone oil that is usefilm in the topical composition of the present invention is dimethicone, although other silicone oils are also within the scope of the invention.

Non-ionic surfactants, which are also commonly referred to in the art as emulsifiers, are used to suspend the silicone oil in the water. A non-ionic surfactant includes a polar end and a non-polar tail. When mixed with water and a hydrophobic (i.e., "water hating") material, such as silicone oil, the non-polar tails of a number of surfactant molecules, which are lipophilic (i.e., "fat loving"), implant themselves into a quantity of the hydrophobic material to form a surfactant-coated droplet of the hydrophobic material. The polar ends of the surfactant molecules, which are hydrophilic (i.e., "water loving"), are exposed to water, a polar molecule, outside of the micelle. The polar ends on the outside of one micelle repel the polar molecules on the outsides of other micelles, causing the micelles to remain suspended in and dispersed throughout the water. As micelles are removed from an aqueous environment, such as the water of the topical composition, by evaporating the water or otherwise, the micelles release the droplet of hydrophobic material. Preferably, the non-ionic surfactants used in the topical composition of the present invention will not re-emulsify silicone oil when exposed to water or an aqueous solution.

The non-ionic surfactants used in the topical composition of the present invention are preferably not irritating to tissues of the body, such as skin. Therefore, the non-ionic surfactants used in the present invention are preferably non-anhydride based. These non-irritating, non-anhydride based, non-ionic surfactants may comprise about 0.01 to about 25% of the weight of the topical composition when used as a component of a wet wipe. Preferably, a combination of two or more non-ionic surfactants makes up about 0.01 to about 2% of the weight of the topical composition and, more preferably, about 0.02 to about 0.2% of the weight of the topical composition.

The topical composition may also have other components, such as preservatives, fragrances, botanical extracts, pH adjusting agents, or antimicrobial agents. Preferably, the topical composition includes at least a synergistic blend of two or more preservatives.

According to another aspect of the present invention, the topical composition is disposed on a sheet to form a wet wipe product. Woven or non-woven sheets of the types known to be useful for forming wet wipes are useful in the wet wipe product of the present invention. The sheet is impregnated or wetted with the topical composition of the present invention to form the wet wipe product.

In another aspect of the invention, the topical composition is applied in a thin layer to skin, the water evaporated from the topical composition, and the silicone oil released onto the skin. The topical composition can be applied to skin directly or by way of a wet wipe including the topical composition. Preferably, upon removal of the micelles of the topical composition from the water by evaporation of the water, the silicone oil is released from all of the micelles onto the skin substantially simultaneously. As the silicone oil is released onto the skin, the silicone oil may form a protective barrier layer on the skin.

Other features and advantages of the present invention will become apparent to those of ordinary skill in the art through a consideration of the ensuing description and the appended claims.

DETAILED DESCRIPTION OF THE INVENTION

According to one aspect, the present invention includes a topical composition with a stable emulsion of water and silicone oil. The silicone oil is suspended in the water with a combination of two or more non-ionic surfactants.

Silicone oil is known in the art to be useful for treating conditions such as dermatitis (e.g., diaper rash) and bed sores. By lubricating skin and by forming a moisture barrier, silicone oils also prevent irritation of skin by prolonged exposure to bodily fluids, such as urine or sweat, and other liquids. Prolonged exposure to bodily fluids or other liquids may occur with the use of diapers or when skin is exposed to moist or wet bedding or clothing for long periods of time.

These benefits of silicone oil may be provided by a topical composition that includes from about 0.1 to about 35% silicone oil by weight. Since silicone oil can leave an oily or greasy feeling residue on the skin, the topical composition of the present invention preferably includes a dilute, yet therapeutic and protective concentration of silicone oil. Accordingly, topical compositions that include less than 3% down to about 0.1% silicone oil by weight of the topical composition are preferred. More preferably, silicone oil comprises less than 3% down to about 1% of the weight of the topical composition. Topical compositions including about 1 to about 2% by weight of the topical composition are even more preferred.

Silicone oils that may be used in the topical composition of the present invention include polydimethylsiloxanes, which are referred to herein and in the art as dimethicones, substituted linear dimethicones, cyclomethicones, dimethiconol, trimethylsiloxysilicate, other silicone oils, and mixtures thereof.

In one embodiment of the topical composition, the silicone oil is NF (National Formulary) grade dimethicone having a honey-like viscosity of about 350 centipoise. Dimethicone is highly insoluble in water.

The topical composition of the present invention also includes one or more non-ionic surfactants. A combination of non-ionic surfactants may be used. As the topical composition is intended primarily for application to skin, the non-ionic surfactants of the topical composition preferably do not irritate the skin. Non-ionic surfactants with alcohol-based polar ends are preferred. In addition, non-anhydride-based surfactants are preferred. Exemplary alcohol-based, non-anhydride-based non-ionic surfactants that are useful in the topical composition of the present invention include, without limitation, polyoxyethylene alcohols, sorbitan esters, and polyoxyethylene sorbate esters, which polyoxyethylene sorbate esters are commonly referred to in the art as "polysorbates".

Polyoxyethylene alcohols that may be employed as at least one of the non-ionic surfactants in the topical composition include, but are not limited to, those known in the art as Laureth 4, Laureth 23, and other laureth, or lauryl alchohol, surfactants. Other polyoxyethylene alcohols that can be used in the topical composition include BRIJ 30SP and BRIJ 35SP, which are ceteth, or cetyl alcohol, surfactants, and other ceteth surfactants.

Exemplary sorbitan esters that can be used in the topical composition of the present invention as at least one of the non-ionic surfactants thereof include, without limiting the scope of the invention, those known in the art as and sold under the trade names ARLACEL 20, ARLACEL 40, and ARLACEL 60, as well as other sorbitan esters.

The polymers known in the art as and sold under the trade names TWEEN 20, TWEEN 40, and TWEEN 60, as well as other polysorbates, may also be used in the topical composition as at least one of the non-ionic surfactants thereof.

As known in the art, every non-ionic surfactant has a hydrophilic-lipophilic balance (hereinafter "HLB") number. Non-ionic surfactants with HLB numbers in the range of about 10 to about 11 are considered in the art to be intermediate. Surfactants having lower HLB numbers are considered in the art to be more hydrophilic, while surfactants having higher HLB numbers are considered in the art to be lipophilic. For example, the sorbitan ester surfactants that are known in the art as ARLACEL surfactants have HLB numbers in the range of 1.8 to 8.6 and are, therefore, said to be hydrophilic non-ionic surfactants. By contrast, the polysorbate surfactants that are known in the art as TWEEN surfactants having HLB numbers in the range of 9.6 to 16.7 are lipophilic surfactants.

To obtain a surfactant system having a desired hydrophilic-lipophilic balance and, thus, a desired HLB number, one non-ionic surfactant can be used or a combination of non-ionic surfactants of differing proportions can be used. The HLB number of the non-ionic surfactant mixture is a weighted average of the HLB numbers of each of the non-ionic surfactants in the mixture. As an example of how combinations of two non-ionic surfactants can be used, each of the following non-ionic surfactant mixtures will provide an HLB number of about 12.6:

50.0% ARLACEL 20 and 50.0% TWEEN 20;
33.5% ARLACEL 40 and 66.5% TWEEN 40;
22.5% ARLACEL 60 and 77.5% TWEEN 60; and
58.0% BRIJ 30SP and 42.0% BRIJ 35SP.

Of course, topical compositions incorporating teachings of the present invention and including combinations of more than two non-ionic surfactants are also within the scope of the present invention.

A combination of non-ionic surfactants that has an HLB number of about 5 to about 16 is useful for emulsifying the silicone oil of the topical composition of the present invention. Preferably, the combination of non-ionic surfactants used to emulsify the silicone oil has an HLB number of about 8 to about 12.

In one embodiment of the topical composition of the present invention, the combination of non-ionic surfactants includes Laureth 4 and Laureth 23. When dimethicone is used as the silicone oil of the topical composition, the proportions of Laureth 4 and Laureth 23 preferably provide an HLB number of about 8 to about 12, a more lipophilic balance, since dimethicone is highly insoluble in water. For example, the weight ratio of Laureth 4 to Laureth 23 can be about 1:1. In this embodiment, the combination of Laureth 4 and Laureth 23 makes up about 0.02 to about 2.0% of the weight of the topical composition.

According to another aspect of the present invention, the topical composition includes preservatives. Preservatives are used in the topical composition to prevent the growth of microorganisms (e.g., bacteria, fungi, yeasts) therein. As the majority of the topical composition is comprised of water, water soluble preservatives are preferably used. Preferably, the preservative must be effective at relatively low concentrations against a broad spectrum of microorganisms. In addition, the preservative must be non-toxic at the required concentration, compatible with other ingredients in the topical composition, stable to the expected preparation and storage conditions, and approved by global regulatory agencies.

The topical composition includes more than one preservative. A blend of preservatives can facilitate a broader spectrum of antimicrobial activity if the individual preservatives of the blend are effective against different microorganisms. Combinations of preservatives may also be capable of killing microorganisms that the individual preservatives could not kill on their own. In addition, in some cases, the total amount of one or more preservatives in the blend can be reduced without reducing the level of antimicrobial activity of that preservative. Finally, due to the presence of multiple preservatives, the microorganisms are less likely to develop resistance to any one of the preservatives in the blend. For these reasons, it can be said that, in the topical composition of the present invention, certain blends of preservatives are synergistic.

In one embodiment of the topical composition of the present invention, the preferred combination of preservatives includes a paraben and sorbic acid or a salt thereof. As an example of a sorbic acid preservative, potassium sorbate can be used to prevent or control the growth of molds and other non-bacterial microorganisms. The parabens prevent or control the growth of bacterial microorganisms. Exemplary parabens that can be used in the topical composition include, but are not limited to, methylparabens, ethylparabens, propylparabens, and butylparabens. Another exemplary preservative that may be employed in the topical composition of the present invention is a mixture of 5-chloro-2-methyl-4-isothiazolin-3-one and 2-methyl-4-isothiazolin-3-one. Other preservatives and mixtures of preservatives may also be used in the topical composition.

The topical composition may also have other components, such as fragrances, botanical extracts, pH adjusting agents, or antimicrobial agents. Fragrances may be added to enhance the appeal of the product to consumers. The fragrances can be water or oil soluble. Botanical extracts may be added to enhance the appeal of the product to consumers, impart a softer feel to the product, or help build healthier skin. The pH of the formulation must be controlled to avoid irritation to the user's skin, extend shelf-life, and generally enhance the product. Without pH adjusting agents, the pH of the topical composition may change over time, especially if there are long periods of time between manufacture and use of the product.

It is preferable to control or maintain the pH of the topical composition of the present invention. The pH of the topical composition is preferably from about 4 to about 8, and more preferably from about 5 to about 7. By maintaining the pH of the topical composition at such levels, irritation to the user's skin can be avoided, the shelf life of the topical composition can be maximized, and the quality of the topical composition can generally be optimized.

Accordingly, the topical composition of the present invention preferably includes a pH adjusting agent. Preferably, the pH adjusting agent used in the topical composition does not irritate or have any other substantial adverse effects on skin. Exemplary pH adjusting agents that can be used in the topical composition include, but are not limited to, acids, such as sorbic acid, citric acid, or benzoic acid, bases, and known buffers. In addition, the salts of weak acids, amines, or any agent capable of adjusting pH without adversely affecting the skin can be used to regulate the pH of the topical composition of the invention.

According to another aspect of the present invention, some components of the topical composition can serve dual roles. For example, some components are useful as pH adjusting agents and preservatives. Alternatively, a component can act as a surfactant and as an antimicrobial agent. In one embodiment of the topical composition of the present invention, potassium sorbate is used as both a pH adjusting agent and as one of the preservatives.

Fragrances can be included in the topical composition to enhance the appeal of the product to consumers. Both water soluble and oil soluble fragrances are useful in the topical composition.

The topical composition can include botanical extracts, which can impart a softer feel to the topical composition or benefit skin.

The following EXAMPLES illustrate, by way of example and not by way of limitation, embodiments of topical compositions within the scope of teachings of the present invention:

EXAMPLE 1

| Ingredient | Range | Optimal |
|---|---|---|
| Dimethicone Oil | 0.1–35% | 1–2% |
| Surfactant | 0.01–25% | 0.02–2.0% |
| Preservatives | 0.005–0.8% | 0.1–0.4% |
| Fragrance | 0.001–5% | 0.1–0.5% |
| Botanical Extracts | 0.001–5% | 0.1–0.5% |
| pH Adjusting Agent | 0.001–4% | 0.01–1% |

EXAMPLE 2

| Category | Ingredient | Percentage |
|---|---|---|
| Water | Purified water | 97.821 |
| Active | Dimethicone | 1.400 |
| Botanical oils and fragrances | | 0.300 |
| Surfactants and emollients | Laureth 4 | 0.070 |
| | Laureth 23 | 0.070 |
| | Propylene glycol | 0.112 |
| Preservatives | 5-chloro-2-methyl-4-isothiazolin-3-one | 0.002 |
| | 2-methyl-4-isothiazolin-3-one | 0.001 |
| | Diazolidinyl urea | 0.060 |
| | Isopropylparaben | 0.004 |
| | Methylparaben | 0.034 |
| | Propylparaben | 0.006 |
| | Potassium sorbate | 0.120 |

The topical composition can be made using a concentrated silicone oil-in-water emulsion composition that includes the non-ionic surfactants. An exemplary concentrated silicone oil-in-water emulsion is a concentrated dimethicone-in-water emulsion that includes 35% dimethicone, 1.75% LAURETH 4, and 1.75% LAURETH 23, each percentage being based on the weight of the emulsion.

An exemplary manner by which the concentrated silicone oil-in-water emulsion can be made includes thoroughly blending the oil and the non-ionic surfactant or surfactants and gradually adding water with sufficient agitation (e.g., high shearing forces) to obtain an homogeneous emulsion. Preferably, the total volume of the concentrated emulsion includes about two volumes of water and one volume of silicone oil.

Preservatives and other components of the topical composition can be added as the concentrated emulsion is being made. For example, lipophilic components of the topical composition can be mixed with the silicone oil prior to mixing the silicone oil and surfactant. Alternatively, lipophilic components may be added to the silicone oil and non-ionic surfactant mixture. As another alternative, lipophilic components can be mixed into the emulsion as the water is being blended into the oil and surfactant mixture or thereafter. As yet another alternative, lipophilic components of the topical composition may be mixed with water prior to adding the water to the silicone oil and non-ionic surfactant mixture or to the emulsion.

The concentrated emulsion can be stored and diluted at a later time. Alternatively, dilution of the concentrated emulsion with water or an aqueous solution can be substantially continuous with the manufacture of the concentrated emulsion. In both cases, the concentrated emulsion is diluted with water to form the topical composition of the present invention. Additional hydrophilic and lipophilic components of the topical composition, such as the blend of preservatives, can be added to the emulsion, either before or after dilution thereof.

Hydrophilic components of the topical composition dissolve into the water, or aqueous solution, portion of the emulsion.

Lipophilic components are preferably emulsified in the composition, either with excess surfactants of the concentrated emulsion or with additional surfactants. Alternatively, lipophilic components can be incorporated into the concentrated emulsion during the manufacture of the concentrated emulsion, wherein the lipophilic components can either dissolve into the silicone oil component of the emulsion, or can be emulsified separately from the silicone oil.

According to another aspect of the present invention, the topical composition is disposed on a sheet to form a wet wipe product. The sheet has pores or voids within which the topical composition can be absorbed. Woven or non-woven sheets of the types known in the art to be useful for forming wet wipes are useful in the wet wipe product of the present invention. Porous, non-woven sheets can be comprised of cellulosic fibrous material, synthetic polymeric fibrous material, or a combination thereof. The sheet is impregnated or wetted with the topical composition of the present invention to form the wet wipe product.

In another aspect of the invention, the topical composition is applied in a thin layer to skin, the water evaporated from the topical composition, and the silicone oil released onto the skin. The topical composition can be applied to skin directly or by way of a wet wipe including the topical composition. Preferably, upon removal of the micelles of the topical composition from the water by evaporation of the water, the silicone oil is released from all of the micelles onto the skin substantially simultaneously. As the silicone oil is released onto the skin, the silicone oil may form a protective barrier layer on the skin.

Alternatively, a thin layer of the topical composition can be applied to skin by spraying a quantity of the topical composition onto the skin, by wiping a quantity of the topical composition onto the skin, or by rubbing a quantity of the topical composition into the skin.

Thus, while certain representative embodiments and details have been shown for purposes of illustrating the invention, it will be apparent to those skilled in the art that various changes in the invention disclosed herein may be made without departing from the scope of the invention, which is defined in the appended claims.

What is claimed is:

1. A wet wipe comprising:
    an emulsion including:
        water;
        silicone oil comprising less than 3% to about 0.1% of the weight of said emulsion; and
        a combination of at least two non-ionic surfactants to emulsify substantially all of said silicone oil in said water;
        a synergistic blend of at least two water soluble preservatives; and
    a sheet wetted with said emulsion.

2. The wet wipe of claim 1, wherein said silicone oil comprises less than 3% to about 1% of the weight of said emulsion.

3. The wet wipe of claim 1, wherein said silicone oil comprises about 1 to about 1.5% of the weight of said emulsion.

4. The wet wipe of claim 1, wherein said silicone oil comprises dimethicone.

5. The wet wipe of claim 4, wherein said dimethicone comprises NF grade dimethicone.

6. The wet wipe of claim 1, wherein each of said at least two non-ionic surfactants comprises a surfactant having a non-anhydride-based chemistry.

7. The wet wipe of claim 1, wherein said at least two non-ionic surfactants comprise at least one hydrophilic surfactant and at least one lipophilic surfactant.

8. The wet wipe of claim 1, wherein said at least two non-ionic surfactants have a hydrophilic-lipophilic balance number of about 5 to about 16.

9. The wet wipe of claim 8, wherein said at least two non-ionic surfactants have a hydrophilic-lipophilic balance number of about 8 to about 12.

10. The wet wipe of claim 8, wherein said at least two non-ionic surfactants have a hydrophilic-lipophilic balance number of about 12.6.

11. The wet wipe of claim 10, wherein each of said at least two non-ionic surfactants is selected from the group consisting essentially of sorbitan esters, polysorbates, and polyoxyethylene alcohols.

12. The wet wipe of claim 1, wherein said at least two non-ionic surfactants comprise Laureth 4 and Laureth 23.

13. The wet wipe of claim 12, wherein said Laureth 4 and said Laureth 23 are included in said emulsion in a weight ratio of about 1:1.

14. The wet wipe of claim 1, wherein said at least two non-ionic surfactants comprise about 0.01% to about 2% of the weight of said emulsion.

15. The wet wipe of claim 1, wherein said at least two non-ionic surfactants comprise about 0.02% to about 0.2% of the weight of said emulsion.

16. The wet wipe of claim 1, wherein said at least two water soluble preservatives comprise about 0.1% to about 0.4% of the weight of said emulsion.

17. The wet wipe of claim 1, wherein said at least two water soluble preservatives are selected from the group comprising sorbic acid or a salt thereof, methyl paraben, ethyl paraben, propyl paraben, butyl paraben, a mixture of 5-chloro-2-methyl-4-isothiazolin-3-one and 2-methyl-4-isothiazolin-3-one, and mixtures thereof.

18. The wet wipe of claim 1, wherein at least one of said preservatives is a pH adjusting agent.

19. The wet wipe of claim 1, further comprising an antimicrobial.

20. A wet wipe comprising:
    an emulsion including:
        water;
        silicone oil comprising less than 3% to about 0.1% of the weight of said emulsion; and
        a plurality of non-ionic surfactants for emulsifying substantially all of said silicone oil in said water, a first of said plurality of non-ionic surfactants comprising a hydrophilic non-ionic surfactant, a second of said plurality of non-ionic surfactants comprising a lipophilic non-ionic surfactant, said plurality of non-ionic surfactants comprising from about 0.01% to about 25% of the weight of said emulsion, said one or more non-ionic surfactants having a combined hydrophilic-lipophilic balance number of from about 5 to about 16; and
    a sheet wetted with said emulsion.

21. The wet wipe of claim 20, wherein said plurality of non-ionic surfactants comprises from about 0.01% to about 2% of the weight of said emulsion.

22. The wet wipe of claim 20, wherein said plurality of non-ionic surfactants comprises from about 0.02% to about 0.2% of the weight of said emulsion.

23. The wet wipe of claim 20, wherein said plurality of non-ionic surfactants has a hydrophilic-lipophilic balance number of from about 8 to about 12.

24. A method of treating or protecting skin, comprising:
wiping the skin with a sheet wetted with a topical composition to transfer a thin layer of said topical composition to the skin, said topical composition comprising:
water;
silicone oil comprising less than 3% to about 0.1% of the weight of said topical composition; and
at least two non-ionic surfactants that emulsify said silicone oil in said water; and
evaporating at least said water from said thin layer to release said silicone oil from said non-ionic surfactants onto the skin.

25. The method of claim 24, wherein said evaporating comprises forming a barrier of said silicone oil on the skin.

26. The method of claim 24, wherein said evaporating comprises substantially simultaneously releasing said silicone oil onto the skin.

* * * * *